United States Patent
Lomas et al.

(10) Patent No.: US 7,169,293 B2
(45) Date of Patent: Jan. 30, 2007

(54) CONTROLLABLE SPACE VELOCITY REACTOR AND PROCESS

(75) Inventors: David A. Lomas, Barrington, IL (US); Lawrence W. Miller, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 523 days.

(21) Appl. No.: 10/327,214

(22) Filed: Dec. 20, 2002

(65) Prior Publication Data

US 2004/0104148 A1 Jun. 3, 2004

Related U.S. Application Data

(60) Continuation-in-part of application No. 10/125,468, filed on Apr. 18, 2002, now Pat. No. 6,869,521, and a continuation-in-part of application No. 09/670,661, filed on Sep. 27, 2000, now abandoned, which is a division of application No. 09/378,416, filed on Aug. 20, 1999, now Pat. No. 6,166,282.

(51) Int. Cl.
*C10G 11/00* (2006.01)
*B01J 8/18* (2006.01)

(52) U.S. Cl. .......................... 208/146; 208/46; 208/76; 208/113; 208/139; 208/152; 208/153; 208/164; 422/141; 422/142; 422/145; 422/147

(58) Field of Classification Search ................. 208/76, 208/152, 164, 113, 46, 139, 146, 153; 422/139, 422/141, 142, 145, 147
See application file for complete search history.

(56) References Cited

U.S. PATENT DOCUMENTS

| | | | |
|---|---|---|---|
| 2,271,148 A | 1/1942 | Becker et al. | 196/52 |
| 2,546,570 A | 3/1951 | Vance, Jr. | 260/449.6 |
| 3,161,583 A | 12/1964 | Pohlenz | 208/164 |
| 3,406,112 A | 10/1968 | Bowles | 208/153 |
| 3,644,199 A | 2/1972 | Evans et al. | 208/120 |
| 3,706,654 A | 12/1972 | Bryson et al. | 208/74 |
| 3,849,291 A | 11/1974 | Owen | 208/78 |
| 3,923,642 A * | 12/1975 | Luckenbach et al. | 208/164 |
| 3,928,483 A | 12/1975 | Chang et al. | 260/668 R |
| 4,025,575 A | 5/1977 | Chang et al. | 260/682 |
| 4,051,013 A | 9/1977 | Strother | 208/78 |
| 4,073,717 A | 2/1978 | Aliev et al. | 208/74 |
| 4,252,479 A | 2/1981 | Scherfenberg | 406/182 |
| 4,447,669 A | 5/1984 | Hamon et al. | 585/640 |
| 4,496,786 A | 1/1985 | Santilli et al. | 585/640 |
| 4,499,314 A | 2/1985 | Seddon et al. | 585/408 |
| 4,547,616 A | 10/1985 | Avidan et al. | 585/640 |

(Continued)

FOREIGN PATENT DOCUMENTS

WO      WO 01/00750 A1      1/1999

*Primary Examiner*—Glenn Caldarola
*Assistant Examiner*—Prem C. Singh
(74) *Attorney, Agent, or Firm*—John G. Tolomei; James C. Paschall

(57) ABSTRACT

Disclosed is an apparatus and process for controlling space velocity in a fluidized catalytic conversion reactor. The catalyst flux rate can be adjusted during the process of the reaction to adjust the space velocity and maintain a fast fluidized flow regime therein. The set parameter in the reactor may be pressure drop which is proportional to catalyst density.

10 Claims, 4 Drawing Sheets

U.S. PATENT DOCUMENTS

| | | | |
|---|---|---|---|
| 4,677,242 A | 6/1987 | Kaiser | 585/638 |
| 4,677,243 A | 6/1987 | Kaiser | 585/638 |
| 4,792,437 A | 12/1988 | Hettinger, Jr. et al. | 422/147 |
| 4,818,372 A | 4/1989 | Mauleon et al. | 208/113 |
| 4,843,183 A | 6/1989 | Inui | 585/640 |
| 4,861,938 A | 8/1989 | Lewis et al. | 585/640 |
| 4,973,792 A | 11/1990 | Lewis et al. | 585/638 |
| 5,095,163 A | 3/1992 | Barger | 585/640 |
| 5,126,308 A | 6/1992 | Barger et al. | 502/214 |
| 5,183,558 A * | 2/1993 | Owen et al. | 208/113 |
| 5,191,141 A | 3/1993 | Barger et al. | 585/640 |
| 5,215,653 A * | 6/1993 | Nelson et al. | 208/152 |
| 5,364,515 A * | 11/1994 | Lomas et al. | 208/113 |
| 5,584,985 A | 12/1996 | Lomas | 208/113 |
| 5,824,208 A * | 10/1998 | Bienstock et al. | 208/76 |
| 6,023,005 A | 2/2000 | Lattner et al. | 585/639 |
| 6,166,282 A | 12/2000 | Miller | 585/638 |
| 2003/0044327 A1 | 3/2003 | Lattner et al. | 422/145 |

* cited by examiner

CONTROLLABLE SPACE VELOCITY REACTOR AND PROCESS

CROSS-REFERENCE TO RELATED APPLICATIONS

This application is a Continuation-In-Part of application Ser. No. 10/125,468 filed Apr. 18, 2002, now U.S. Pat. No. 6,869,521 and a Continuation-In-Part of application Ser. No. 09/670,661 filed Sep. 27, 2000, now abandoned, which is a Division of application Ser. No. 09/378,416 filed Aug. 20, 1999, now U.S. Pat. No. 6,166,282, the contents of which applications are hereby incorporated by reference in their entireties.

FIELD OF THE INVENTION

The present invention relates generally to a catalytic conversion reactor and process utilizing a catalytic reaction zone with a controllable space velocity.

BACKGROUND OF THE INVENTION

In many catalytic reactions, it is important that reactants be well mixed with catalyst to afford sufficient opportunity for the reactant to contact the catalyst. Fluidized reactors have been designed to ensure adequate mixing of catalyst and reactants. Fluidized reactors are designed to ensure that the reactants are in contact with the catalyst for sufficient time to allow for the reaction to proceed. However, in many catalyzed reactions the reactants should not remain in contact with catalyst too long or overconversion can occur which can generate undesirable byproducts and degrade product quality. This is especially true when the reaction involves hydrocarbons of which overreaction can cause excess generation of coke, inhibiting catalyst activity and selectivity.

Space velocity typically referred to as weight hourly space velocity (WHSV) is crucial to ensuring that reactants and catalyst are in contact for the optimal duration. Space velocity is a reaction condition that is important when rapid reaction times are involved such as monomolecular catalytic cracking reactions or rapid catalytic conversion reactions. The catalyst and reactants need to make contact, but excessive contact time will cause additional undesirable reaction to occur. Space velocity is calculated by Formula 1:

$$WHSV = \frac{M_f}{m_c} \quad (1)$$

where WHSV is the weight hourly space velocity, $M_f$ is the mass flow rate of feed to the reactor and $m_c$ is the mass of catalyst in the reactor. Space time is the inverse of space velocity. The mass of catalyst, $m_c$, can be determined by Formula 2:

$$m_c = \frac{\Delta P \cdot V}{h} \quad (2)$$

where $\Delta P$ is the pressure drop over the height, h, of the reactor and V is the volume of the reactor. The ratio of pressure drop and height is the catalyst density in the reactor:

$$\rho_c = \frac{\Delta P}{h} \quad (3)$$

Hence, combining Formulas 2 and 3:

$$m_c = \rho_c \cdot V \quad (4)$$

Accordingly, both density, $\rho_c$, and space velocity, WHSV, are functions of pressure drop, $\Delta P$. From Formula 4, the relationship of space velocity and volume is shown in Formula 5:

$$WHSV = \frac{M_f}{\rho_c V} \quad (5)$$

Catalyst flux is determined by Formula 6:

$$\omega_c = \frac{M_c}{A} \quad (6)$$

where $\omega_c$ is catalyst flux, $M_c$ is the mass flow rate of catalyst and A is the cross sectional area of the reactor. Additionally the product of height, h, and cross-sectional area, A, when constant, of the reactor is the reactor volume, V:

$$V = h \cdot A \quad (7)$$

The mass flow rate of feed, $M_f$, to the reactor is calculated by Formula 8:

$$M_f = v_f \rho_f A \quad (8)$$

where $v_f$ is the superficial gas velocity of the feed, $\rho_f$ is the density of the feed and A is the cross sectional area of the reactor at which the velocity is measured. Hence, substituting Formulas 2, 7 and 8 into Formula 1 for constant cross-sectional reactor area yields formula 9:

$$WHSV = \frac{v_f \rho_f}{\Delta P} \quad (9)$$

Residence time is a reaction condition that is important when the reaction is not as rapid. The catalyst and reactants need to soak together to ensure catalyst and reactants are in contact and for a sufficient period of time to allow the reaction to occur. Residence time, $T_r$, is calculated by Formula 10:

$$T_r = \frac{V}{Q_f} \quad (10)$$

where $Q_f$ is the actual volumetric flow rate of feed at reactor process conditions of temperature and pressure. The volumetric flow rate, $Q_f$, to the reactor is calculated by Formula 11:

$$Q_f = v_f A \quad (11)$$

Substituting Formulas 7 and 11 into Formula 10 for constant cross-sectional reactor area yields:

$$T_r = \frac{h}{v_f} \quad (12)$$

In a fluidized catalytic reactor, the flow characteristics may be considered to assure space velocity or residence time is optimal.

Two types of fluidization regimes typically used in fluidized catalytic reactors are a transport flow regime and a bubbling bed. Transport flow regimes are typically used in FCC riser reactors. In transport flow, the difference in the velocity of the gas and the catalyst, called the slip velocity, is relatively low, typically less than 0.3 m/s (1.0 ft/s) with little catalyst back mixing or hold up. Slip velocity is calculated by formula 9:

$$v_s = \frac{v_f}{\varepsilon} - v_c \quad (13)$$

where $v_s$ is the slip velocity, $v_f$ is the superficial gas velocity of the feed, $v_c$ is the catalyst velocity and $\varepsilon$ is the void fraction of the catalyst. Another way to characterize flow regimes is by slip ratio which is the ratio of actual density in the flow zone to the non-slip catalyst density in the flow zone. The non-slip catalyst density is calculated by the ratio of catalyst flux to the superficial gas velocity as in formula 10:

$$\rho_{cns} = \frac{\omega_c}{v_f} \quad (14)$$

where $\rho_{cns}$ is the non-slip catalyst density in the flow zone, $\omega_c$ flux of the catalyst and $v_f$ is the superficial gas velocity of the feed. The slip ratio is proportional to the hold up of catalyst in the flow zone. Typically, a slip ratio for a transport flow regime does not reach 2.5. Consequently, the catalyst in the reaction zone maintains flow at a low density and very dilute phase conditions. The superficial gas velocity in transport flow is typically greater than 3.7 m/s (12.0 ft/s), and the density of the catalyst is typically no more than 48 kg/m³ (3 lb/ft³) depending on the characteristics and flow rate of the catalyst and vapor. In transport mode, the catalyst-vapor mixture is homogeneous without vapor voids or bubbles forming in the catalyst phase.

Fluidized bubbling bed catalytic reactors are also known. In a bubbling bed, fluidizing vapor forms bubbles that ascend through a discernible top surface of a dense catalyst bed. Only catalyst entrained in the vapor exits the reactor with the vapor. The superficial velocity of the vapor is typically less than 0.5 m/s (1.5 ft/s) and the density of the dense bed is typically greater than 480 kg/m³ (30 lb/ft³) depending on the characteristics of the catalyst. The mixture of catalyst and vapor is heterogeneous with pervasive vapor bypassing of catalyst.

Intermediate of dense, bubbling beds and dilute, transport flow regimes are turbulent beds and fast fluidized regimes. U.S. Pat. No. 4,547,616 discloses a turbulent bed used in a reactor for converting oxygenates to olefins. In a turbulent bed, the mixture of catalyst and vapor is not homogeneous. The turbulent bed is a dense catalyst bed with elongated voids of vapor forming within the catalyst phase and a less discernible surface. Entrained catalyst leaves the bed with the vapor, and the catalyst density is not quite proportional to its elevation within the reactor. The superficial velocity is between about 0.5 and about 1.3 m/s (1.5 and 4.0 ft/s), and the density is typically between about 320 and about 480 kg/m³ (20 and 30 lb/ft³) in a turbulent bed.

U.S. Pat. No. 6,166,282 discloses a fast fluidized flow regime for oxygenate conversion. Fast fluidization defines a condition of fluidized solid particles lying between the turbulent bed of particles and complete particle transport mode. A fast fluidized condition is characterized by a fluidizing gas velocity higher than that of a dense phase turbulent bed, resulting in a lower catalyst density and vigorous solid/gas contacting. In a fast fluidized zone, there is a net transport of catalyst caused by the upward flow of fluidizing gas. The superficial combustion gas velocity for a fast fluidized flow regime is conventionally believed to be between about 1.1 and about 2.1 m/s (3.5 and 7 ft/s) and the density is typically between about 48 and about 320 kg/m³ (3 and 20 lb/ft³). Catalyst exits the reaction zone a small amount slower than the vapor exiting the reaction zone. Hence, for a fast fluidized flow regime the slip velocity is typically greater than or equal to 0.3 m/s (1.0 ft/s) and the slip ratio is greater than or equal to 2.5 for most FCC catalysts. Fast fluidized regimes have been used in FCC combustors for regenerating catalyst and in coal gasification.

The conversion of hydrocarbon oxygenates to olefinic hydrocarbon mixtures is accomplished in a fluidized catalytic reactor. Such oxygenates to olefins reactions are rapidly catalyzed by molecular sieves such as a microporous crystalline zeolite and non-zeolitic catalysts, particularly silicoaluminophosphates (SAPO). Numerous patents describe this process for various types of these catalysts: U.S. Pat. Nos. 3,928,483; 4,025,575; 4,252,479; 4,496,786; 4,547,616; 4,677,243; 4,843,183; 4,499,314; 4,447,669; 5,095,163; 5,191,141; 5,126,308; 4,973,792 and 4,861,938.

The oxygenates to olefins catalytic process may be generally conducted in the presence of one or more diluents which may be present in the hydrocarbon oxygenate feed in an amount between about 1 and about 99 mol-%, based on the total number of moles of all feed and diluent components fed to the reaction zone (or catalyst). Diluents include, but are not limited to, helium, argon, nitrogen, carbon monoxide, carbon dioxide, hydrogen, water, and hydrocarbons such as methane, paraffins, aromatic compounds, or mixtures thereof. U.S. Pat. Nos. 4,861,938 and 4,677,242 particularly emphasize the use of a diluent combined with the feed to the reaction zone to maintain sufficient catalyst selectivity toward the production of light olefin products, particularly ethylene.

U.S. Pat. No. 6,023,005 discloses a method for selectively converting hydrocarbon oxygenates to light olefins in which desirable carbonaceous deposits are maintained on the total reaction volume of catalyst by regenerating only a portion of the total reaction volume of catalyst and mixing the regenerated portion with the unregenerated total reaction volume of catalyst. The method incorporates a fluidized catalytic bed reactor with continuous regeneration. In a preferred arrangement, the oxygenate feed is mixed with regenerated catalyst and coked catalyst at the bottom of a riser and the mixture is lifted to a disengaging zone. In the disengaging zone, coked catalyst is separated from the gaseous materials by means of gravity or cyclone separators. A portion of the coked catalyst to be regenerated is sent to a stripping zone to recover adsorbed hydrocarbons. Stripped spent catalyst is passed to a regenerator.

U.S. Pat. No. 4,547,616 discloses an improvement in a process for the conversion of hydrocarbon oxygenates to olefins by the operation of a turbulent bed at elevated temperatures and controlled catalyst activity. The turbulent bed is maintained in a vertical reactor column to achieve good mixing at a velocity greater than the dense bed transition velocity to a turbulent regime and less than transport velocity for the average catalyst particle. The superficial fluid velocity is disclosed in a range between about 0.3 to 2 meters per second. Provision is made for passing partially regenerated catalyst to the reactor fluidized bed of catalyst beneath the upper interface and sufficiently below to achieve good mixing in the fluid bed.

Another typical fluidized catalytic reaction is a fluidized catalytic cracking (FCC) process. An FCC process is carried out by contacting the starting material whether it be vacuum gas oil, reduced crude, or another source of relatively high boiling hydrocarbons with a catalyst made up of finely divided or particulate solid material. The catalyst is fluidly transported by passing gas through it at sufficient velocity to produce a transport flow regime. Contact of the oil with the fluidized catalytic material catalyzes the cracking reaction. The cracking reaction deposits coke on the catalyst. Catalyst exiting the reaction zone is spoken of as being "spent", i.e., partially deactivated by the deposition of coke upon the catalyst. Coke is comprised of hydrogen and carbon and can include other materials in trace quantities such as sulfur and metals that enter the process with the starting material. Coke interferes with the catalytic activity of the spent catalyst by blocking acid sites on the catalyst surface where the cracking reactions take place. Spent catalyst is traditionally transferred to a stripper that removes adsorbed hydrocarbons and gases from catalyst and then to a regenerator for purposes of removing the coke by oxidation with an oxygen-containing gas. The regenerator may operate with a bubbling bed, turbulent bed or fast fluidized flow regime. Such regenerators using a fast flow regime are called combustors. However, in a regenerator or combustor, coke is burned from the catalyst. The catalyst does not provide a catalytic function other than with regard to oxidation. An inventory of catalyst having a reduced coke content, relative to the spent catalyst in the stripper, hereinafter referred to as regenerated catalyst, is collected for return to the reaction zone. Oxidizing the coke from the catalyst surface releases a large amount of heat, a portion of which escapes the regenerator with gaseous products of coke oxidation generally referred to as flue gas. The balance of the heat leaves the regenerator with the regenerated catalyst. The fluidized catalyst is continuously circulated between the reaction zone and the regeneration zone. The fluidized catalyst, as well as providing a catalytic function in the reaction zone, acts as a vehicle for the transfer of heat from zone to zone. The FCC processes, as well as separation devices used therein are fully described in U.S. Pat. Nos. 5,584,985 and 4,792,437. Specific details of the various reaction zones, regeneration zones, and stripping zones along with arrangements for conveying the catalyst between the various zones are well known to those skilled in the art.

The FCC reactor catalytically and thermally cracks gas oil or heavier feeds into a broad range of products. Cracked vapors from the FCC unit enter a separation zone, typically in the form of a main column, that provides a gas stream, a gasoline cut, light cycle oil (LCO) and clarified oil (CO) which includes heavy cycle oil (HCO) components. The gas stream may include dry gas, i.e., hydrogen and $C_1$ and $C_2$ hydrocarbons, and liquefied petroleum gas ("LPG"), i.e., $C_3$ and $C_4$ hydrocarbons. The gasoline cut may include light, medium and heavy gasoline components. A major component of the heavy gasoline fraction comprises condensed single ring aromatics. A major component of LCO is condensed bicyclic ring aromatics.

Subjecting product fractions to additional reactions is useful for upgrading FCC product quality. The recracking of heavy product fractions from an initially cracked FCC product is one example. Typically, in recracking, cracked effluent from a riser of an FCC reactor is recontacted with catalyst at a second location to cleave larger molecules down into smaller molecules. For example, U.S. Pat. No. 4,051,013 discloses cracking both gasoline-range feed and gas oil feed in the same riser at different elevations. Such reactions are relatively rapid. WO 01/00750 A1 discloses introducing gasoline feed and FCC feed at different elevations in a riser reactor, separating the cracked product and recycling portions thereof back to the same riser reactor. Other types of reactions to upgrade FCC product fractions are less rapid.

The above-described hydrocarbon catalytic conversion processes are sensitive to underreaction and overreaction which both degrade product quality. Use of a fast fluidized flow regime assures thorough mixing of catalyst and feed to catalyze the reaction. Hence, we sought to provide an improved fluidized non-oxidative catalytic hydrocarbon conversion process and apparatus that can provide a fast fluidized flow regime at adjustable flow conditions that will enhance the conversion to the desired products. Additionally, we sought to provide a reactor that can accommodate the varying demands on space velocity and residence time based on different feed composition and desired products.

SUMMARY OF THE INVENTION

We have discovered a reactor and process for controlling space velocity in a fluidized catalytic reactor. Catalyst density in a fast fluidized flow regime is sensitive to catalyst flux. Space velocity is a function of catalyst density. Therefore, it is possible to adjust the catalyst circulation rate to achieve the desired space velocity to effect catalyst to feed contacting at highly effective gas-solid, mixing conditions. Moreover, the catalyst circulation rate can be controlled based on the pressure drop in the reactor to maintain or achieve a desired space velocity.

DETAILED DESCRIPTION OF THE INVENTION

We have discovered a catalytic reactor that can be used to obtain thorough mixing of fluid reactants and particulate catalyst while contacting the catalyst and fluid reactants together for an adjustably optimal time. Hence, desirable reactions may occur without underreacting or overreacting to degrade the quality of the product composition for varying feeds and varying reactions. For example, in a fluidized catalytic reactor for upgrading naphtha that may be obtained from an FCC cut, we have found that better mixing between the feed and the catalyst promotes (hydrogen transfer reactions and catalytic cracking reactions while reducing the undesirable generation of coke and dry gas. Use of a fast fluidized catalytic conversion zone provides such thorough mixing. We have also found that in catalytic conversion of a hydrocarbon oxygenates to olefins, use of a fast fluidized zone significantly reduces catalyst inventory compared to dense fluidized catalytic reactions. However, we have found that maintaining a fast fluidized reaction zone may be difficult. Fast fluidized combustion zones have been attempted in combustors for oxidizing coked catalyst from an FCC reactor zone but such combustors do not involve nonoxidative catalytic conversion. The main concern in a combustion zone is that the catalyst has sufficient residence time to burn off all of the coke. Fluidized catalytic conversion reactors particularly hydrocarbon catalytic conversion processes bring with it other flow considerations because the feed is the primary fluidization medium and the reactant that is undergoing catalytic conversion to recoverable product. The selectivity and conversion of the gas phase reaction must be optimized. Selectivity and conversion are functions of temperature, residence time and space velocity. As indicated by Formulas 1 and 5, space velocity is related to both catalyst and reactant feed flow rates and reactor volume. Formula 11 indicates that residence time is related to reactor volume. Hence, this invention gives greater consideration to the flow characteristics, space velocity and residence time in a fluidized catalytic conversion reactor. Controlling these flow characteristics provides for achieving and maintaining a desired fluidization regime, particularly a fast fluidized flow regime.

The present invention may be described with reference to a fluidized catalytic reactor 10 shown in FIG. 1. Although many configurations of the present invention are possible, one specific embodiment is presented herein by way of example. All other possible embodiments for carrying out the present invention are considered within the scope of the present invention.

Figure 1:
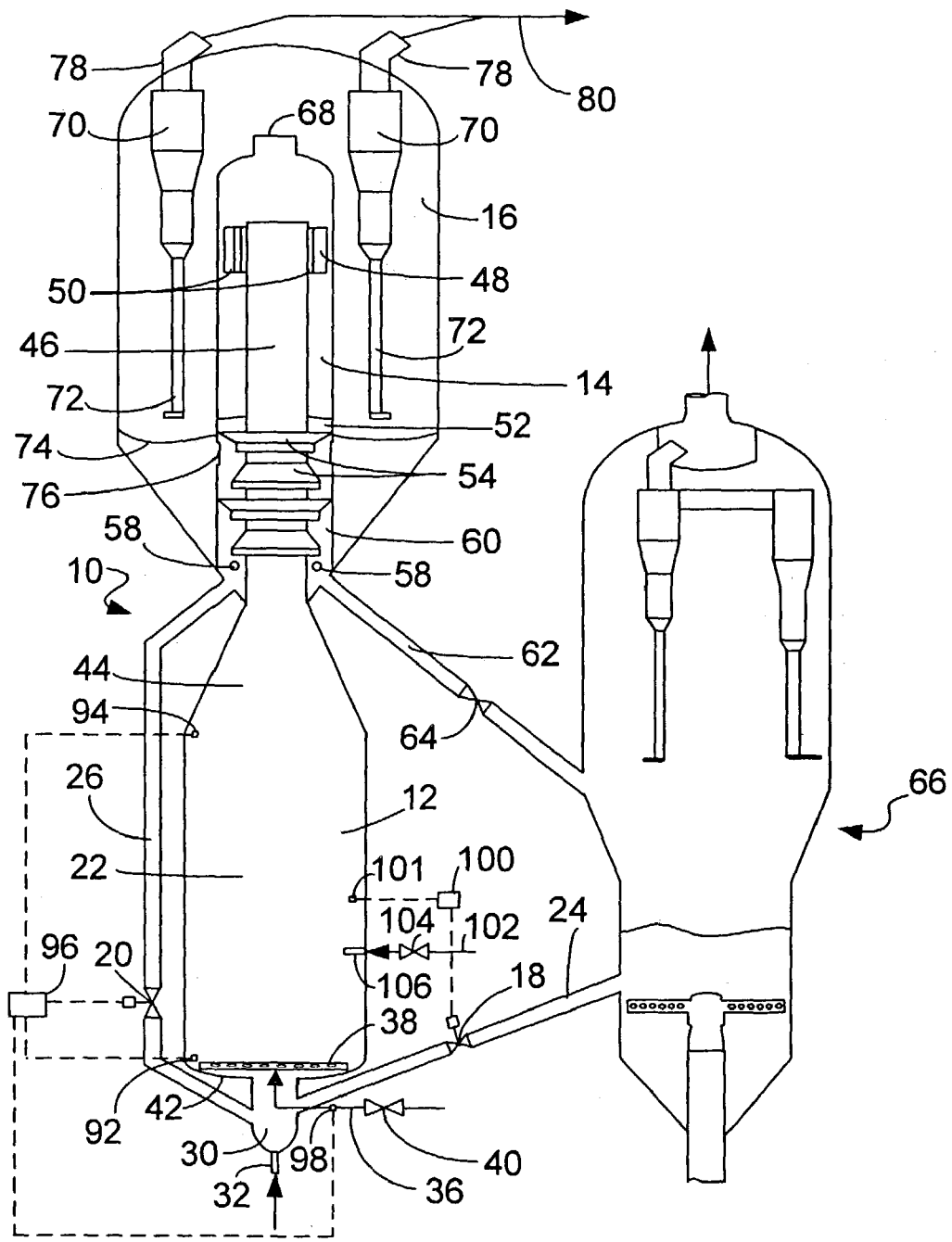
FIG. 1 is a schematic drawing of a fluidized catalytic reactor for use in the present invention.

In the embodiment of the present invention in FIG. 1, the catalytic reactor 10 comprises a reactor section 12 and a separation section 16 that may include a disengaging section 14. The contacting of feed and catalyst occurs in the reactor section 12 of the catalytic reactor 10. Control valves 18, 20 govern the rate of catalyst circulation to the reactor section 12. The control valve 18 governs the flow rate of regenerated catalyst from a catalyst regenerator 66 through a regenerated catalyst pipe 24 to the reactor section 12, and the control valve 20 governs the flow rate of recycled catalyst through a recycle spent catalyst pipe 26 to the reactor section 12. The catalyst flow rate through one or both of the control valves 18 and/or 20 is inversely proportional to the space velocity of reactants through the reactor section 12. Relative settings of the control valves 18, 20 are independently adjusted also to obtain the desired temperature and mixture of the catalyst in the reactor section 12 that will contact the reactant feed. The multiple recycle spent catalyst pipes 26 may be used to increase catalyst flux, and the recycle spent catalyst pipes 26 may extend through the reactor 10 and particularly the reactor section 12.

In an embodiment, the regenerated catalyst from the regenerated catalyst pipe 24 and the recycled catalyst from the recycle spent catalyst pipe 26 are mixed in a mixing pot 30 of the reactor section 12. A minimally reactive or non-reactive diluent, such as steam, is distributed to the mixing pot 30 through a nozzle 32 to mix the regenerated and recycled catalyst before it contacts the feed. The mixing pot 30 enables adequate mixing and temperature equilibration of recycled and regenerated catalyst before it is introduced to the feed. This assures that the hot regenerated catalyst is moderated to a lower temperature by thorough mixing and direct heat exchange with the cooler recycled catalyst which has not been heated by regeneration. All or a part of the hot regenerated catalyst could cause thermal cracking or other undesirable byproduct generation if it were allowed to contact the feed reactants without first undergoing thorough moderation. In an embodiment which does not utilize a catalyst regenerator, the mixing pot 30 may not be necessary.

Feed reactants which may include hydrocarbons are introduced through a line 36 to a distributor 38 which distributes feed to the reactor section 12. The feed may be liquid that is vaporized in the reactor or vapor, in embodiments. The flow rate of feed through the line 36 is governed by a control valve 40. The setting of the control valve 40 also influences the space velocity and residence time. The feed rate to the reactor section 12 is directly proportional to the space velocity and inversely proportional to residence time.

Feed reactants from the distributor 38 contact fluidized catalyst ascending upwardly from the mixing pot 30. The feed reactants may also include diluent as is necessary to provide appropriate catalytic reaction conditions. In an embodiment, the feed reactants fluidize the ascending catalyst to generate a fast fluidized bed in a catalytic reaction zone 22 of the reactor section 12. It may be in practice that a dense bed forms at a base 42 of the reactor section 12 below the level at which all of the catalyst is fluidized by the incoming feed reactants in the catalytic reaction zone 22. In an embodiment, the catalytic reaction zone 22 extends between the distributor 38 and a top region 44, although catalytic activity may occur outside of the catalytic reaction zone 22. The top region 44 of the reactor section 12 has a cross-sectional area that decreases proportionally with height. The top region 44 may take the form of a frusto-conical section. The reducing cross-sectional area of the top region 44 serves to accelerate the mixture of fluidized product and catalyst toward transport mode as they exit the reactor section 12 and enter the transport conduit 46. The transport conduit 46 communicates the reactor section 12 with the disengaging section 14. The transport conduit 46 may take the form of a riser. The transport conduit 46 should have a smaller cross-sectional area than the reactor section 12. Consequently, upon leaving the catalytic reaction zone 22 and the reactor section 12, the product fluids and spent catalyst accelerate into a transport mode, thus giving the spent catalyst and product fluids less time to further react or crack into undesirable products. Entering transport mode also prevents catalyst from falling out of entrainment with the product fluids.

Spent catalyst and product ascend from the reactor section 12 through the transport conduit 46 to the disengaging section 14. The spent catalyst and vapor product exit through discharge openings 48 (only one shown) in swirl tubes 50 to effect a primary, centripetal separation of spent mixed catalyst from the vapor product. Separated spent mixed catalyst settles into a dense bed 52 in the disengaging section 14. The spent mixed catalyst in the dense bed 52 is then in an embodiment stripped over a series of baffles 54 by use of a stripping medium such as steam entering through stripping nozzles 58 in a stripping section 60 of the disengaging section 14. In an embodiment, a first portion of the stripped spent catalyst exits the disengaging section 14 through a spent catalyst pipe 62 at a flow rate that may be governed by a control valve 64. The stripped spent catalyst may be delivered to the regenerator 66. The regenerator 66 may be shared with another fluidized catalytic system, such as an FCC system, in an embodiment. Alternatively, the spent catalyst pipe 62 may deliver spent catalyst to another reactor. A second portion of the stripped spent catalyst is withdrawn through the recycle spent catalyst pipe 26 at a flow rate governed by the control valve 20 and is delivered to the mixing pot 30 where it is mixed with regenerated catalyst delivered from the regenerated catalyst pipe 24. Product vapors and entrained spent catalyst exit from the disengaging section 14 through an outlet 68 to the separation section 16 that contains at least one cyclone separator 70. Alternatively, the separator section could comprise one or more cyclone separators 70 external to the disengaging section 14 and with an inlet directly connected to the outlet 68 and a dipleg 72 directly connected to the disengaging section 14 or the reactor section 12 by appropriate conduits. In an embodiment, the outlet 68 may be directly connected to the cyclone separators 70. The entrained spent catalyst is centripetally separated from product vapors in the cyclone separators 70. Separated catalyst exits through the dipleg 72 into a dense catalyst bed 74 which may be fluidized (not shown). In an embodiment, spent catalyst in the dense catalyst bed 74 enters into the stripping section 60 of the disengaging section 14 through ports 76. Alternatively, the spent catalyst in the dense catalyst bed 74 may be removed through the pipes 26, 62 without undergoing stripping. Product fluids are withdrawn from the cyclone separators 70 through outlet conduits 78 and are recovered in a line 80.

Referring to the reactor 10 of the present invention shown in FIG. 1, the space velocity may be changed in the reactor section 12 by increasing or decreasing the rate of delivery of catalyst to the reactor section 12. This can be done by adjusting the control valve 20 to change the flow rate of spent catalyst through the recycle spent catalyst pipe 26 into the mixing pot 30 and/or adjusting the control valve 18 to change the flow rate of regenerated catalyst through the regenerated catalyst pipe 24 into the mixing pot 30 of the reactor section 12. Increasing the catalyst flow rate through one or both of the control valves 18, 20 into the reactor section 12 decreases the weight hourly space velocity in the reactor section 12 while decreasing the flow rate through one or both of the control valves 18, 20 increases the weight hourly space velocity. The total flow rate of catalyst to the reactor section 12 through the pipes 24, 26 is directly proportional to catalyst flux.

Another way to control the weight hourly space velocity is to increase or decrease the feed flow rate through the control valve 40 on the feed line 36. Increase of the feed flow rate is directly related to the superficial velocity ($v_f$). However, the feed flow rate is typically left constant.

Lower superficial gas velocities have a greater tendency to generate a dense bed as catalyst flux increases; whereas, higher superficial gas velocities have a lower tendency to generate a dense bed as catalyst flux increases. The desired fast-fluidized flow regime in which the greatest degree of mixing of catalyst and reactant occurs is moderated between a dense bed condition at about 320 kg/m$^3$ (20 lb/ft$^3$) and a transport flow regime at about 48 kg/m$^3$ (3 lb/ft$^3$). It is more difficult to maintain a fast-fluidized flow at lower superficial gas velocity because the catalyst tends to choke the reactant gas fed to the reactor, thereby jumping from a transport flow regime to a dense bed. Furthermore, at extremely high superficial gas velocities, no increase in catalyst flux will bring the flow regime out of transport. We have determined that a fast fluidized flow regime can be maintained under the present invention with superficial velocities as low as about 1.3 m/s (4 ft/s) and as high as about 9.1 m/s (30 ft/s), which is higher than conventionally used, and with catalyst fluxes as low as about 15 kg/m$^2$s (2.8 lb/ft$^2$s) and as high as about 1100 kg/m$^2$s (204.5 lb/ft$^2$s). In an embodiment, a very controllable fast fluidized regime can be maintained under the present invention with superficial velocities as low as about 1.5 m/s (5 ft/s) and as high as about 5 m/s (16 ft/s) and with catalyst fluxes as low as about 30 kg/m$^2$s (5.6 lb/ft$^2$s) and as high as about 325 kg/m$^2$s (60.4 lb/ft$^2$s). Under these conditions, catalyst flux can be increased or decreased to increase or decrease the space velocity without disrupting the flow regime such that it chokes to a dense bed or accelerates into a transport flow regime.

The subject invention is useful in a catalytic conversion reactor in which catalyst is fluidized either by a fluidized feed or by a fluidizing diluent or both. Typically, the fluidized feed has sufficient superficial velocity to entrain the catalyst or fluidize the catalyst as it enters into the reactor. In an embodiment of the present invention, the addition of diluent can be controlled to adjust the degree of fluidization in the reactor.

The space velocity in the reactor section 12 may be controlled as follows. The pressure drop between two elevations in the reactor section 12 may be measured to monitor catalyst density in the reactor, weight hourly space velocity or other reactor condition that is proportional to space velocity. When desired to adjust the space velocity, either to maintain or attain the fast-fluidized regime, to change resulting conversion or selectivity or to accommodate a different feed composition, the control valve 20 can be opened relatively more or less to change the catalyst flux which changes the space velocity accordingly.

FIG. 1 illustrates a control scheme for effectuating adjustments to space velocity. A pressure sensor 92 is located at a relatively low elevation in the reactor section 12, and a pressure sensor 94 is located at a relatively high elevation in the reactor section 12. In an embodiment, at least one of the sensors, preferably the lower pressure sensor 92, should be in the catalytic reaction zone 22. The pressure sensors 92, 94 transmit a pressure signal and/or other data to a controller 96, which may comprise a pressure differential controller. A sensor 98 which may be on the line 36 or on the control valve 40 determines the flow rate of feed therethrough by a suitable device and signals data to the controller 96. With the data, the controller 96 determines the mass flow rate of feed to the reactor 10 through the control valve 40 and the mass of catalyst in the reactor section 12 from which the weight hourly space velocity is determined. The flow rate of feed may be constant. The current weight hourly space velocity or a parameter proportional thereto is compared to a set point which can be adjusted. If the space velocity or proportional parameter does not match the set point, the controller 96 signals the control valve 20 to open relatively more to lower the space velocity or to open relatively less to increase the space velocity.

The temperature of the recycled spent catalyst in the recycle spent catalyst pipe 26 is similar to the temperature in the reactor section 12. Hence, temperature in the reactor section 12 is controlled by the flow rate of hot regenerated catalyst in the regenerated catalyst pipe 24 through the control valve 18. A temperature sensor 101 in the catalytic reaction zone 22 or the reactor section 12 signal temperature data to a controller 100 which may be a temperature indicator controller. The controller 100 compares the temperature in the reactor section 12 to an adjustable set point temperature and signals the control valve 18 to open relatively more if the reactor temperature is lower than the set point or to open relatively less if the reactor temperature is higher than the set point. Suitable types, operation and locations of sensors and controller(s) may vary consistently with ordinary skill in the art and the description herein.

The volume of the catalytic reaction zone 22 is proportional to residence time and inversely proportional to space velocity as indicated by Formulas 5 and 10. The volume of the catalytic reaction zone 22 may be adjusted and therefore residence time and space velocity may be adjusted in the catalytic reaction zone 22 by adjusting the flow rate of a minimally reactive or non-reactive diluent to the reactor section 12. Additional diluent may be added to the reactor section 12 by a diluent line 102 at a rate governed by a control valve 104 through a nozzle 106. The effective reactor volume can be changed by adjusting the diluent rate to the reactor section 12 through the nozzle 106. If a smaller effective reactor volume is desired to provide a smaller residence time or a larger space velocity, the control valve 104 should be opened relatively more to allow a greater volumetric flow rate of diluent to the reactor section 12 from the diluent line 102. If a larger effective reactor volume is desired to increase residence time or reduce space velocity, the control valve 104 should be opened relatively less to allow a smaller volumetric flow rate of diluent to the reactor section 12 from the line 102. Steam is a suitable diluent.

Figure 2:
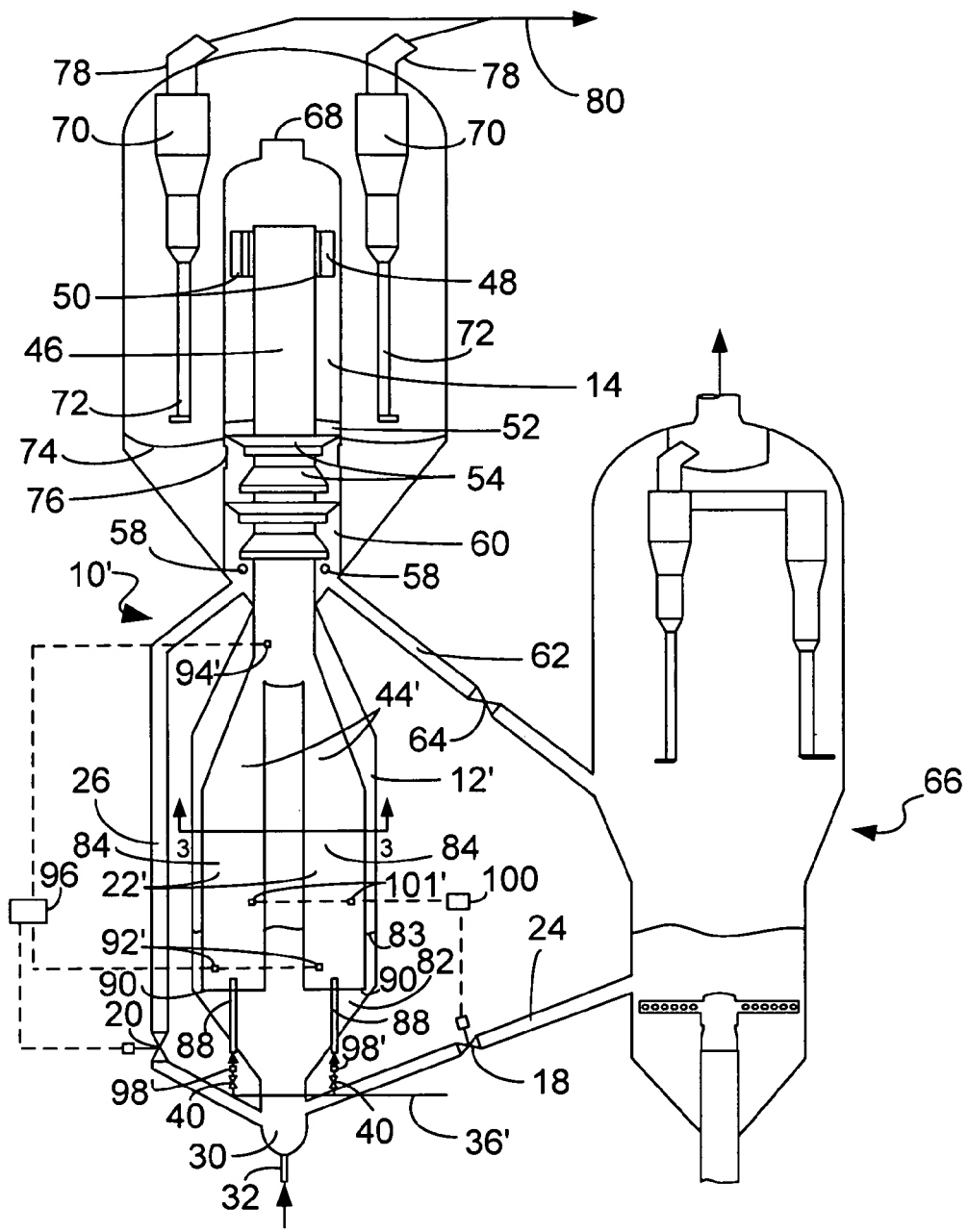
FIG. 2 is a schematic drawing of an alternative embodiment of the present invention.

FIG. 2 shows another embodiment of the present invention which could be used to replace the reactor section 12 in FIG. 1. All elements in FIG. 2 that are not modified from FIG. 1 retain the same reference numeral designation. Although one reactor section 12' may be used for carrying out the purposes of this invention, the provision of a plurality of reactor subsections 84 with dedicated nozzles 88 and control valves 40' to govern the flow rate of feed to each of the reactor subsections 84 may offer flexibility over use of a single reactor section 12. A plurality of the reactor subsections 84 within a single reactor section 12' provides a greater degree of control of residence time and space velocity. The embodiment in FIG. 2 provides greater flexibility because the cross sectional area, and, therefore, the volume of a catalytic reaction zone 22' are adjustable. Reactor cross-sectional area is inversely proportional to superficial gas velocity. Superficial gas velocity is inversely proportional to residence time and directly proportional to space velocity. Hence, residence time which is directly proportional to cross-sectional area and space velocity which is inversely proportional to cross-sectional reactor area may be modified by adjusting the flow rate or shutting off flow to one of the reactor subsections 84. The same relationship applies to the reactor subsections 84 that do not have a constant cross-sectional area because the volume of the catalytic reaction zone is proportional to residence time and inversely proportional to space velocity as shown in Formulas 5 and 10.

Reactant feed is distributed by a line 36' at a flow rate governed by the control valves 40' through the nozzles 88 to the respective reactor subsections 84 in the reactor section 12'. The reactor subsections 84 may be tubular with an open bottom end 90 communicating with a dense catalyst bed 82 that forms in the reactor section 12'. Feed entering the reactor subsections 84 preferably pulls catalyst from the dense catalyst bed 82 into the reactor subsections 84 where contacting occurs. The amount of catalyst pulled into the reactor subsection 84 for a given flow rate of feed in the nozzle 88 will be proportional to the superficial velocity of the feed and the height of a catalyst level 83 of the dense catalyst bed 82 which is controlled by the control valves 18, 20. Hence, the ratio of catalyst to feed, catalyst density, catalyst flux, space velocity, and residence time in the reactor subsections 84, and therefore the reactor section 12', can all be controlled by adjusting the elevation of the catalyst level 83 of the dense catalyst bed 82 and/or adjusting or eliminating the flow rate of the feed through one or more of the control valves 40'.

The catalytic reaction zone 22' comprises the reactor subsection 84 from the bottom end 90 to a top region 44'. In an embodiment, the catalytic reaction zone 22' comprises all of the reactor subsections 84 to which feed is distributed. The top region 44' of each of the reactor subsections 84 has a reduced cross-sectional area that may take the form of frustoconical or partial frustoconical sections. The reduced cross-sectional area of the top region 44' serves to accelerate the mixture of vapor product and spent mixed catalyst as they exit the reactor subsection 84. In an embodiment that is not shown, the top regions 44' may communicate with outlet conduits which communicate the reactor subsections 84 with the transport conduit 46. In such an embodiment, the outlet conduits should all have a smaller cross-sectional area than the respective reactor subsection 84 and the transport conduit 46.

Figure 3:
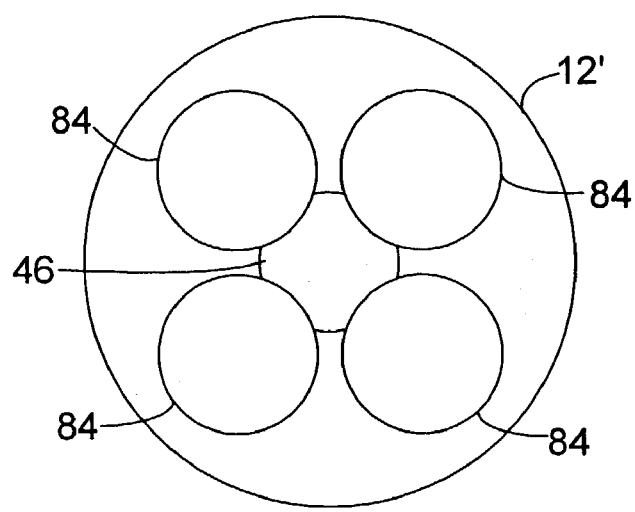
FIG. 3 is a cross-sectional view taken along segment 3—3 in FIG. 2.
Figure 4:
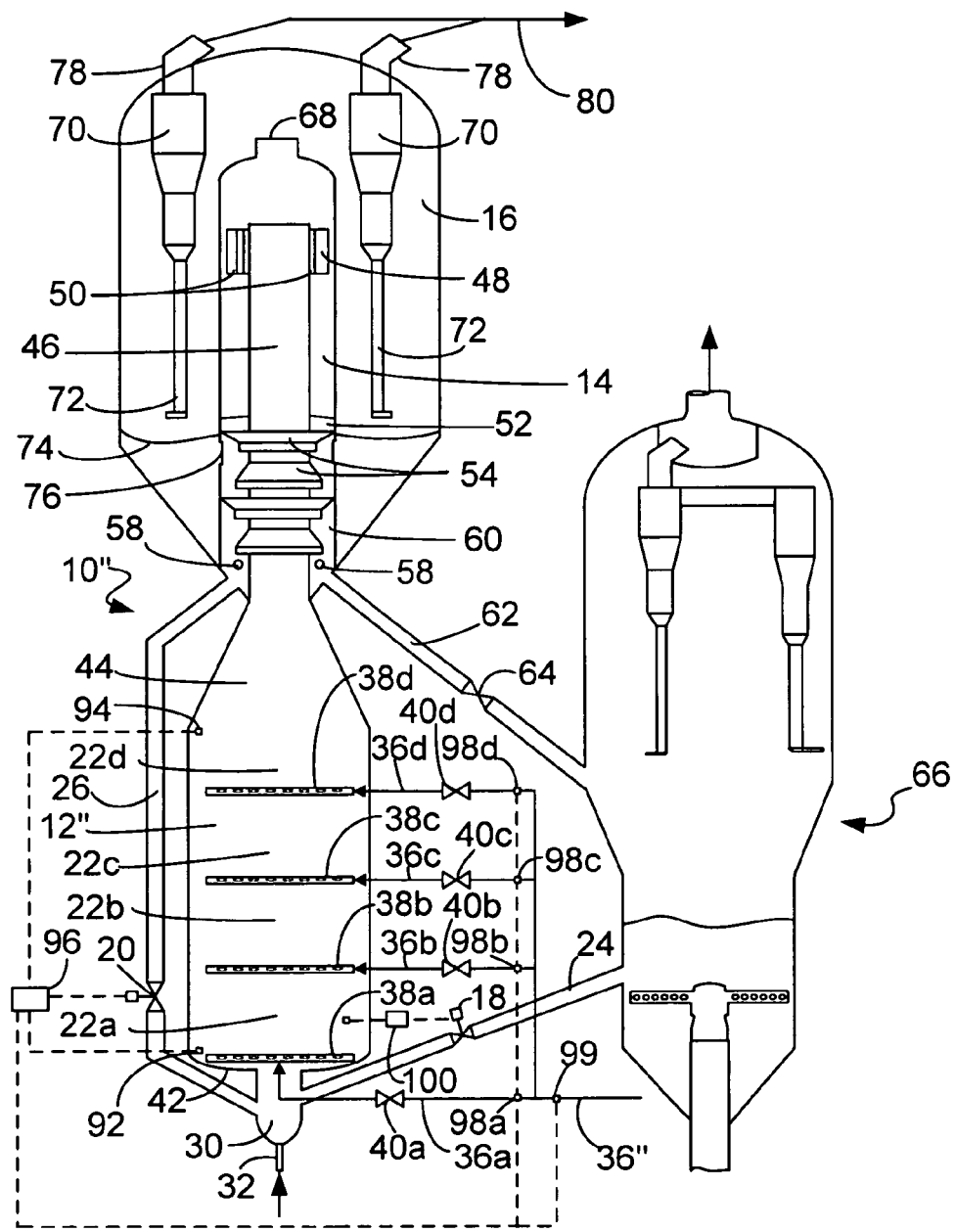
FIG. 4 is a schematic drawing of a further alternative embodiment of the present invention.

FIG. 3 is an upwardly looking cross-sectional view taken along segment 3—3 of the reactor section 12'. Although, four reactor subsections 84 are shown in FIGS. 3 and 4, the invention contemplates more or less, but more than one reactor subsection 84. In an embodiment, the reactor subsections 84 may share common walls. In the embodiment shown in FIGS. 2 and 3, a cross-sectional area of the transport conduit 46 may be less than the aggregate cross-sectional area of all of the reactor subsections 84 that feed the transport conduit 46. Additionally, in an embodiment, the cross-sectional area of the transport conduit 46 may be less than that of a single reactor subsection 84, so that all but one of the reactor subsections 84 may be shut off. Consequently, upon leaving the reactor subsection 84, the product vapor and spent mixed catalyst accelerate into a transport mode through the top region 44', thus giving the spent catalyst and product vapor little time to further react or crack into undesirable products. Entering transport mode also prevents catalyst from falling out of entrainment with the product vapor.

The alternative embodiment of a reactor 10' of the present invention may be operated similarly to the reactor 10, but greater flexibility is offered. The aggregate volume of catalytic reaction zone 22' of the reactor section 12 comprising the on-stream reactor subsections 84 may be varied which is an additional way to adjust the space velocity and the residence time. For instance, by cutting off flow through two of the control valves 40' to two respective reactor subsections 84, the volume of the catalytic reaction zone 22' is halved. The change in volume will cancel out according to Formula 9. However, the halved cross-sectional area will double the superficial velocity for the reactant feed at the constant flow rate through the line 36'. Moreover, because the catalyst brought into the reactor subsections 84 is dependent on the flow of feed thereto which has doubled for each reactor subsection remaining on-stream, the overall catalyst flux will not substantially change. The doubled superficial velocity will draw double the catalyst flux into each of the two reactor subsections 84 to compensate for the two reactor subsections 84 that have been shut off at the control valves 40'. Hence, the weight hourly space velocity will increase. Similarly, the change in volume cancels out in Formula 12 while the velocity doubles. Consequently, the shutting off of flow through the control valves 40' to two reactor subsections 84 results in a halving of the residence time in the reactor subsections 84.

Additionally, space velocity may be controlled by adjusting the catalyst flux as in the reactor 10. The pressure drop between two elevations in the catalytic reaction zone 22' of the reactor section 12 may be measured to monitor catalyst density in the reactor and weight hourly space velocity. When desired to adjust the space velocity or a parameter proportional thereto, without changing the flow rate through either of control valves 40', the control valve 20 can be opened relatively more or less to change the height of the catalyst level 83. The height of the catalyst level 83 is proportional to the amount of catalyst flux pulled into the reactor subsections 84 which changes the space velocity accordingly. FIG. 2 illustrates a control scheme for effectuating adjustments to space velocity by changing flux. A pressure sensor 92' is located at a relatively low elevation in the catalytic reaction zone 22 of each of the reactor subsections 84 or at least in the one reactor subsection 84 that will always be on-stream, preferably above the nozzle 88. A pressure sensor 94' is located at a relatively high elevation in the reactor section 12', in an embodiment, at a location where all of the outlets of the reactor subsections 84 converge, such as in the transport conduit 46, or in a single reactor subsection 84 that will always be on-stream. The pressure sensors 92', 94' transmit a pressure signal and/or other data to the controller 96, which may comprise a pressure differential controller. Sensors 98' on each of the branch lines from the line 36', on each control valve 40', on each of the nozzles 88 or on the line 36' determine the flow rate of feed to the reactor section 12 by a suitable device and signals data to the controller 96. With the data, the controller 96 determines the mass flow rate of feed to the reactor 10 and the mass of catalyst in the catalytic reaction zone 22' comprising the on-stream reactor subsections 84 from which the weight hourly space velocity is determined. The flow rate of feed through the line 36' may be constant. The actual weight hourly space velocity in the reactor section 12 is compared to a set point which can be adjusted. If the space velocity does not match the set point, the controller 96 signals the control valve 20 to open relatively more to lower the space velocity or to open relatively less to increase the space velocity. Temperature in the reactor section 12 is controlled by the flow rate of hot regenerated catalyst in the regenerated catalyst pipe 24 through the control valve 18. Temperature sensors 101 in the catalytic reaction zone 22' signal temperature data to the controller 100 which may be a temperature indicator controller. The temperature sensor 98' may instead be in the dense catalyst bed 82 in the reactor section 12'. The controller 100 compares the temperature in the reactor section 12' to a set point temperature and signals the control valve 18 to open relatively more if the reactor temperature is lower than the set point or to open relatively less if the reactor temperature is higher than the set point. Locations of sensors, operation of controller(s) may vary consistent with ordinary skill in the art and the description herein.

Some or all of the reactor subsections 84 may be operated under different conditions, such as temperature, space velocity or residence time to achieve the desired reactor flow conditions and product composition. Similarly, superficial feed velocity in one, some or all of the reactor subsections 84 may be different. Under this embodiment, the lower pressure sensors 92' will have to be in each reactor subsection 84 and the upper pressure sensor 94' will have to be where all outlets of reactor subsections converge or in each reactor subsection 84. Moreover, under this embodiment, the sensors 98' will have to be on each branch of the line 36' or on each of the control valves 40'.

FIG. 4 shows another embodiment of the present invention which could be used to replace the reactor section 12 in FIG. 1 or 12' in FIG. 2. All elements in FIG. 4 that are not modified from FIG. 1 retain the same reference numeral designation. A reactor section 12" of FIG. 4 includes a plurality of reactant feed distributors 38a–38d all at different heights in the reactor section 12". Although four reactant feed distributors 38a–38d may be used for carrying out the purposes of this invention, more or less may be used, but more than one. Each reactant feed distributor 38a–38d is fed by a respective feed line 36a–36d in communication with a main feed line 36". A plurality of control valves 40a–40d are each dedicated to less than all of the plurality of reactant feed distributors 38a–38d to separately govern the flow of feed to the plurality of reactant feed distributors. In an embodiment, each control valve 40a–40d is dedicated to each respective reactant feed distributor 38a–38d and feed line 36a–36d to separately govern the flow rate of reactant feed therethrough. A sensor 99 which may be on the main feed line 36" or sensors 98a–98d which may be on the respective lines 36a–36d or on the respective control valves 40a–40d determines the flow rate of feed therethrough by a suitable device and signals data to the controller 96. A catalytic reaction zone 22a–22d is the volume in the reactor section 12" that is above the respective reactant feed distributor 38a–38d up to the top region 44. In the reactor section 12", the reactor volume of the catalytic reaction zone 22a–22d is inversely proportional to the elevation of the reactant feed distributor 38a–38d.

The provision of a plurality of the reactant feed distributors 38a–38d with the dedicated control valves 40a–40d to govern the flow rate of feed to the reactor section 12 may offer flexibility over use of a single reactant feed distributor to control residence time and space velocity. The embodiment in FIG. 4 provides greater flexibility because the volume of the catalytic reaction zone 22a–22d is adjustable. Formula 5 indicates that space velocity is inversely proportional to reactor volume. Formula 10 indicates that residence time is directly proportional to reactor volume. Although there will be a catalyst density gradient over the reactor height which will change with the changing height of the distribution of the reactant stream, the reactor volume of the catalytic reaction zone will change more significantly upon a change in feed distributor elevation.

If it is desired to reduce the residence time and/or increase the space velocity in the reactor section 12', the flow to the lower reactant feed distributor 38a–38c through the dedicated control valve 40a–40c would be shut off and flow to the higher reactant feed distributor 38b–38d through the dedicated control valve 40b–40d would be opened. Similarly, if it is desired to increase the residence time and/or decrease the space velocity in the reactor section 12', the flow to the higher reactant feed distributor 38b–38d through the dedicated control valve 40b–40d would be shut off and flow to the lower reactant feed distributor 38a–38c through the dedicated control valve 40a–40c would be opened.

The top region 44 of the reactor sections 12" have a reduced cross-sectional area that may take the form of frustoconical section. The reduced cross-sectional area of the top region 44 serves to accelerate the mixture of vapor product and spent mixed catalyst as they exit the reactor section 12". Consequently, upon leaving the reactor subsection 84, the product vapor and spent mixed catalyst accelerate into a transport mode through the top region 44, thus giving the spent catalyst and product vapor less time to further react or crack into undesirable products. Entering transport mode also prevents catalyst from falling out of entrainment with the product vapor.

Additionally, space velocity may be controlled by adjusting the catalyst flux as in the reactor 10. The pressure drop between two elevations in the catalytic reaction zone 22a–22d of the reactor section 12 may be measured to monitor catalyst density in the reactor and weight hourly space velocity. When desired to adjust the space velocity or a parameter proportional thereto, without changing the elevation of the operating reactant feed distributor 38a–38d, the control valve 20 can be opened relatively more or less to change the catalyst flux to the reactor section 12″ which changes the space velocity accordingly. FIG. 4 illustrates a control scheme for effectuating adjustments to space velocity by changing flux which is similar to that for FIG. 1. Although only one is shown, the pressure sensors 92′ will be located at a point slightly above every reactant feed distributor 38a–38d in the respective reaction zone 22a–22d. The pressure sensor 94 is located at a relatively high elevation in the reactor section 12′. The pressure sensors 92′, 94′ transmit pressure signals and/or other data to the controller 96, which may comprise a pressure differential controller. The sensor 99 determines the flow rate of feed through to the applicable reactant feed distributor 38a–38d by a suitable device and signals data to the controller 96. With the data, the controller 96 determines the mass flow rate of feed to the reactor 10 through the reactant feed distributors 38a–38d and the mass of catalyst in the reactor section 12 from which the weight hourly space velocity is determined. The flow rate of feed through the line 36″ may be constant. The actual weight hourly space velocity in the reactor section 12″ is compared to a set point which can be adjusted. If the space velocity does not match the set point, the controller 96 signals the control valve 20 to open relatively more to lower the space velocity or to open relatively less to increase the space velocity to come closer to the desired space velocity. Temperature in the reactor section 12 is controlled by the flow rate of hot regenerated catalyst in the regenerated catalyst pipe 24 through the control valve 18 based on a signal from a temperature sensor (not shown) in the catalytic reaction zone 22a–22d to the controller 100 similar to the control scheme shown in FIG. 1. Suitable locations, types and operation of sensors and controller(s) may vary consistent with ordinary skill in the art and the description herein.

It is also contemplated that one or more distributors 38a–38d may operate at the same time at the same or different flow rates to provide desired benefits. Additionally, if diluent through the nozzle 32 is not sufficient to fluidize catalyst up to the higher reactant feed distributor 38a–38d, a lower distributor may have to always operate to some degree to fluidize catalyst up to the primarily operational reactant feed distributor 38a–38d. Lastly, a retractable distributor (not shown) or a transport conduit with a telescopically retractable inlet end (not shown) may be used to accomplish the present invention.

Accordingly, the present invention provides for the adjustment of reactor flow parameters of residence time, volume and space velocity to meet particular needs in response to differences in feed composition or desired product slate and to achieve and maintain an appropriate fluidization regime.

What is claimed is:

1. A process of catalytically reacting a feed by contacting it with catalyst particles at a controlled space velocity, said process comprising:

delivering catalyst particles to a reactor section at a rate sufficient to provide a catalyst flux of between about 15 and about 1100 $kg/m^2s$ and a catalyst density in the reactor section between 48 and 320 $kg/in^3$ upon fluidization;

distributing a reactant stream to said reactor section at a rate sufficient to provide a superficial velocity of between about 1 m/s and about 9 m/s, that will fluidize the catalyst particles and contact the reactant stream with catalyst particles, contacting said catalyst particles with said reactant stream;

catalyzing the conversion of the reactant stream to a product stream;

withdrawing catalyst particles and product fluid, including said product stream, from the reactor;

separating said catalyst particles from said product fluid;

recycling said catalyst particles which have not been regenerated as recycled catalyst particles to said reactor section; and mixing said recycled catalyst particles with regenerated catalyst particles before said regenerated catalyst particles contact said reactant stream.

2. The process of claim 1 further including adjusting a space velocity in the reactor section.

3. The process of claim 2 wherein the space velocity is adjusted by adjusting the catalyst flux in the reactor section.

4. The process of claim 3 wherein the catalyst flux is adjusted based on the catalyst density in the reactor section.

5. The process of claim 1 wherein the space velocity is adjusting by adjusting a volume of a catalytic reaction zone in said reactor section.

6. The process of claim 1 wherein the catalyst flux is between about 25 and about 300 $kg/m^2s$.

7. The process of claim 1 wherein the superficial velocity is between about 1.5 and about 5 m/s.

8. A process of catalytically reacting a feed by contacting it with catalyst particles, said process comprising:

delivering catalyst particles to a reactor section at a catalyst circulation rate to provide a catalyst flux sufficient to provide a catalyst density in the reactor section upon fluidization;

distributing a reactant stream to the reactor section at a rate sufficient to fluidize the catalyst particles and contact the reactant stream with catalyst particles;

contacting said catalyst particles with said reactant stream;

catalyzing the conversion of the reactant stream to a product stream;

measuring a pressure drop in said reactor section;

controlling the catalyst circulation rate in response to the pressure drop in the reactor section; and withdrawing catalyst particles and said product stream from the reactor section.

9. The process of claim 8 wherein a reactant stream is distributed to at least one of a plurality of reactor subsections in the reactor section and changing the reactor subsections to which a reactant stream is distributed.

10. The process of claim 8 wherein an additional catalyst circulation rate of regenerated catalyst particles to said reactor section is controlled in response to a temperature in the reactor section.

* * * * *